(12) United States Patent
La Barrie et al.

(10) Patent No.: US 11,867,708 B2
(45) Date of Patent: Jan. 9, 2024

(54) AUTOMATIC QUALITY CHECK FOR LABORATORY INSTRUMENTS

(71) Applicant: Beckman Coulter, Inc., Brea, CA (US)

(72) Inventors: Madhuri La Barrie, Miami, FL (US); Scott Lendzian, Miami, FL (US); Joanna Selinsky, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 323 days.

(21) Appl. No.: 16/534,296

(22) Filed: Aug. 7, 2019

(65) Prior Publication Data
US 2020/0049723 A1    Feb. 13, 2020

Related U.S. Application Data (60) Provisional application No. 62/717,475, filed on Aug. 10, 2018.

(51) Int. Cl.
*G01N 35/00* (2006.01)
*G01N 33/48* (2006.01)

(52) U.S. Cl.
CPC . *G01N 35/00623* (2013.01); *G01N 35/00693* (2013.01); *G01N 35/00732* (2013.01);
(Continued)

(58) Field of Classification Search
None
See application file for complete search history.

(56) References Cited

U.S. PATENT DOCUMENTS

| 5,096,669 A * | 3/1992 | Lauks | B01L 3/502715 |
| | | | 324/438 |
| 6,579,717 B1 * | 6/2003 | Matsubara | G01N 35/026 |
| | | | 198/349.5 |

(Continued)

FOREIGN PATENT DOCUMENTS

| WO | WO-2016195894 A1 | 12/2016 |
| WO | WO-2020033509 A1 | 2/2020 |

OTHER PUBLICATIONS

"International Application Serial No. PCT/US2019/045450, International Search Report dated Nov. 14, 2019", 5 pgs.

(Continued)

*Primary Examiner* — P. Kathryn Wright
*Assistant Examiner* — Curtis A Thompson
(74) *Attorney, Agent, or Firm* — Schwegman Lundberg & Woessner, P.A.

(57) ABSTRACT

Systems and methods for calibrating laboratory instruments. In an example, a laboratory instrument for testing patient specimens includes a testing apparatus configured to receive a cassette that includes a patient specimen or a quality control specimen. In response to determining that a quality control specimen is present, the instrument obtains a first measurement of a parameter. If the first parameter is outside an expected tolerance, the instrument ceases performing tests on all specimens, the instrument re-tests the quality control specimen to obtain a second measurement of the parameter. If the second measurement is within the expected tolerance, instrument resumes processing of the cassette. If the second measurement is outside the expected tolerance, the instrument indicates that recalibration or service is required.

8 Claims, 8 Drawing Sheets

(52) U.S. Cl.
CPC ............. *G01N 33/48* (2013.01); *G01N 35/00* (2013.01); *G01N 35/00871* (2013.01); *G01N 2035/00752* (2013.01)

(56) References Cited

U.S. PATENT DOCUMENTS

| | | | | |
|---|---|---|---|---|
| 2009/0150083 | A1* | 6/2009 | Odachi | G01N 35/00613 702/19 |
| 2012/0179405 | A1* | 7/2012 | Yano | G01N 35/02 702/85 |
| 2013/0078617 | A1* | 3/2013 | Ueda | G01N 35/00623 435/5 |
| 2013/0316461 | A1* | 11/2013 | Fujita | G01N 33/5005 436/63 |
| 2013/0333490 | A1* | 12/2013 | Tanoue | G01N 1/10 348/135 |
| 2013/0337493 | A1* | 12/2013 | Hansteen | G01N 31/00 436/171 |
| 2016/0356800 | A1* | 12/2016 | Glavina | G16H 10/40 |
| 2019/0276871 | A1* | 9/2019 | Stern | C12Q 1/20 |
| 2019/0383842 | A1* | 12/2019 | Saito | G01N 35/0092 |
| 2021/0025907 | A1* | 1/2021 | Hirabayashi | G01N 35/00623 |

OTHER PUBLICATIONS

"International Application Serial No. PCT/US2019/045450, Written Opinion dated Nov. 14, 2019", 6 pgs.

Alere Technologies, et al., "Afinion HbA1c Dx Test System", Alere Executive Summary prepared for the FDA Clinical Chemistry and Clinical Toxicology Devices Panel, [Online] Retrieved from the Internet on Apr. 4, 2019: <URL: https://www.fda.gov/downloads/AdvisoryCommittees/CommitteesMeetingMaterials/Medical Devices/MedicalDevicesAdvisoryCommittee/ClinicalChemistryandClinicalToxicologyDevices Panel/UCM511598.pd>. (Jul. 22, 2016), 127 pgs.

"International Application Serial No. PCT/US2019/045450, International Preliminary Report on Patentability dated Feb. 25, 2021", 8 pgs.

* cited by examiner

AUTOMATIC QUALITY CHECK FOR LABORATORY INSTRUMENTS

CLAIM FOR PRIORITY

This patent application claims the benefit of priority to U.S. Provisional Application Ser. No. 62/717,475, filed Aug. 10, 2018, which is incorporated by reference herein in its entirety.

BACKGROUND

Laboratory instruments can perform automated analysis of patient specimens such as blood or urine. In order to ensure accurate results, laboratory instruments undergo periodic quality control procedures. For example, if a quality control fails on a particular instrument, then the instrument goes offline until adjustments are made and an additional quality control test passes.

Existing solutions can cause laboratory downtime while troubleshooting and retesting takes place. For example, handling a quality control failure often requires determining which instrument failed from a set of instruments, retrieving the quality control specimen from inside the instrument, and running additional testing procedures. During this process, if the instrument continues to run, potentially erroneous data may be collected.

Additionally, work cells, or interconnected laboratory instruments, may pose additional challenges for quality control testing. For example, a first instrument may execute a quality control test but continue to process patient specimens before the quality control testing result is obtained. If a failing quality control testing result is obtained, several patient specimens from the same cassette may have already been tested and transferred to a second instrument or possibly to an output buffer, and possibly erroneous results might have been made available to the laboratory technician, Laboratory Information System, or clinician.

Hence, new solutions are needed to automate quality control testing of laboratory instruments to improve the quality of results and to improve efficiency.

BRIEF SUMMARY

Systems and methods for testing patient specimens are disclosed. In an aspect, a laboratory instrument includes a testing apparatus configured to receive a cassette including a patient specimen or a quality control specimen and perform testing on specimens, and a processor configured to perform operations. The operations include, in response to determining that the cassette includes a quality control specimen. The operations include causing the testing apparatus to cease performing tests on patient specimens. The operations include causing the testing apparatus to test the quality control specimen to obtain a first measurement of a parameter. The operations include in response to determining that the first measurement is outside an expected tolerance, causing the testing apparatus to test the quality control specimen to obtain a second measurement. The operations include in response to determining the second measurement is either within the expected tolerance and restarting processing of patient specimens or outside the expected tolerance and causing the testing apparatus to continue to cease performing tests on patient specimens.

In an aspect, the processor is further configured to send an alert.

In an aspect, determining that the cassette includes a quality control specimen includes reading a bar code or other identifying indicia on the quality control specimen.

In an aspect, causing the testing apparatus to test the quality control specimen further includes aspirating, by the laboratory instrument, the quality control specimen, and obtaining the first measurement of the parameter.

In an aspect, the processor is further configured to determine that the cassette includes a quality control specimen and a patient specimen, cause the testing apparatus to eject the cassette, and cause an alert to be displayed on a display device.

In an aspect, the processor is further configured to cause the testing apparatus to cease processing of further cassettes and specimens, and allow specimens that are undergoing processing to continue processing.

In an aspect, the processor is further configured to cause the testing apparatus to receive an additional cassette including a patient specimen.

In an aspect, the processor is further configured to the testing apparatus to process the patient specimen to obtain an additional result, and provide the additional result to a display on the laboratory instrument.

In an aspect, the processor is further configured in response to determining that the first measurement is outside an expected tolerance, cause an alert to be activated on the laboratory instrument.

In an aspect, work cell system includes a first laboratory instrument configured to receive, from an input buffer, a cassette including one or more patient specimens or quality control specimens, perform a first test on the specimens, and pass the cassette to a second laboratory instrument. The second laboratory instrument is configured to receive the cassette from the first laboratory instrument and perform an operation on the specimens. The work cell further includes a processor configured to determine that that the cassette is received at the first laboratory instrument and includes a quality control specimen. The processor is further configured to cause the first laboratory instrument to cease processing of specimens, to cause the first laboratory instrument to test the quality control specimen to obtain a first measurement of a parameter, in response to determining that the first measurement of the parameter is outside an expected tolerance, activating an alert and cause the first laboratory instrument to test the quality control specimen to obtain a second measurement. The processor is further configured to, in response to determining the second measurement is either within the expected tolerance, restart processing of patient specimens. The processor is further configured to, in response to determining that the second measurement is outside the expected tolerance, cause the first laboratory instrument to continue to cease performing tests on patient specimens.

In an aspect, the processor is further configured to send an alert.

In an aspect, the processor is further configured to determine that the cassette includes quality control specimens includes reading a bar code or other identifying indicia on the quality control specimen.

In an aspect, causing the first laboratory instrument to test the quality control specimen further includes aspirating, by the laboratory instrument, the quality control specimen, and obtaining the first measurement of the parameter.

In an aspect, the processor is further configured to determine that the cassette includes a quality control specimen and a patient specimen, cause the work cell system to eject the cassette, and display an alert on a display device.

In an aspect, the processor is further configured to cause the first and second laboratory instruments to cease processing of further cassettes and specimens, and allow specimens that are undergoing processing to continue processing.

In an aspect, the processor is further configured to cause the first laboratory instrument to receive an additional cassette including a patient specimen, cause the first laboratory instrument to process the patient specimen to obtain an additional result, cause the first laboratory instrument to provide the patient specimen to the second laboratory instrument, cause the second laboratory instrument to process the patient specimen to obtain an second additional result, and provide the additional result and the second additional result to a display device.

In an aspect, a method for quality control of a hematology laboratory instrument is disclosed. The method includes: determining that a cassette includes a quality control specimen, ceasing performing tests on patient specimens, testing the quality control specimen to obtain a first measurement of a parameter, in response to determining that the first measurement is outside an expected tolerance, testing the quality control specimen to obtain a second measurement, and in response to determining the second measurement is either (i) within the expected tolerance and restarting processing of the cassette, or (ii) outside the expected tolerance and continuing to cease performing tests on specimens.

In an aspect, the method further includes sending an alert.

In an aspect, determining that the cassette includes a quality control specimen includes reading a bar code or other identifying indicia on the quality control specimen.

In an aspect, the method further includes determining that the cassette includes a quality control specimen and a patient specimen, ejecting the cassette, and displaying an alert on a display device.

In an aspect, the method further includes allowing specimens that are undergoing processing to continue processing.

The aspects described herein can be implemented on laboratory instruments, using methods, or by a processor executing computer program instructions that are stored on non-transitory computer-readable media.

A better understanding of the nature and advantages of embodiments of the present invention may be gained with reference to the following detailed description and the accompanying drawings.

DETAILED DESCRIPTION

Aspects described herein relate generally to laboratory instruments. Examples of laboratory instruments are hematology testing instruments, flow cytometry instruments, particle counters, and combinations thereof. More particularly, aspects described herein automatically detect a quality control failure, restart the failing quality control test, and cease processing of patient specimens (samples) of a laboratory instrument pending retesting of the quality control specimen.

Aspects described herein provide technical improvements in the field of laboratory instrument testing. For example, by automatically re-running quality controls that have failed the first time, the disclosed system can reduce the probability of releasing patient specimen test results to a Laboratory Information System (LIS), patient or clinician if the patient specimen was tested by an instrument that failed a quality control test. Further, because many quality control tests pass upon retesting, the disclosed system obviates the need to manually isolate and reprocess quality control specimens, search for a cassette that contains the failing quality control specimen, or isolate the failing instrument from a set of instruments. Accordingly, aspects increase laboratory uptime and efficiency.

Quality control testing ensures that the obtained testing results are within a tolerance range. A quality control test typically involves testing a known specimen for which an expected outcome is known. Erroneous results can be caused by a variety of variable factors such as humidity, temperature, erroneous testing specimens, instrument wear, or instrument age. Testing can be periodically performed or performed on demand. For example, a technician may perform a quality control test at the start of each work day or each work shift. Alternatively, a quality control test may be initiated after a specified number of patient specimens have been tested. Instruments may be recalibrated prior to retesting or as a result of a failed test.

Aspects described herein also perform quality control on instruments within work cells, or sets of interconnected instruments. Quality control testing can occur on each interconnected instrument within a work cell. Work cells can include several instruments in series and/or groups of instruments in parallel. For example, a work cell can include a first, a second, and a third instrument. The first instrument can perform a first test whereas the second and third instruments each perform a second test. Therefore, a given patient specimen may be provided by the first instrument to either the second or the third instrument.

Examples of instruments include hematology analyzers or a Slide Maker Stainer (SMS). An SMS can perform an operation such as preparing a slide for medical examination. But the disclosed solutions apply to other kinds of laboratory instruments. In an aspect, a patient specimen may only be processed by the SMS if the specimen failed on the hematology analyzer.

If a quality control test fails on a first instrument, then testing patient specimens on that instrument can lead to erroneous results. In some cases, multiple specimens may need to be retested, for example, specimens that were tested immediately prior to the quality control failing and have since been moved to an output buffer or a different instrument. Additionally, due to the use of cassettes, which can include multiple specimens, testing a single cassette of specimens on an instrument that has failed a quality control test can cause multiple specimen retests.

Disclosed solutions minimize delay in retesting patient specimens due to failed quality control. For example, if the delay in retesting is significant, the specimens may not be suitable for retesting, potentially requiring the acquisition of a new specimen from the patient. In outpatient settings, or if the patient has been discharged from inpatient care, recalling the patient to obtain a new specimen can be time-consuming and expensive for both the clinician and the patient. Aspects can also detect mixed cassettes and eject the cassettes so that the quality control specimen can be separated from patient specimens.

The following non-limiting example is introduced for illustrative purposes. It should be understood, however, that this disclosure is envisioned for use on a single instrument as well as within multiple linked instruments. In one specific example, several instruments are configured in a work cell to execute in series such that patient specimens are passed from one instrument to another. Patient specimens are loaded into cassettes, each of which can include multiple specimens. Each cassette is introduced in turn to a first instrument.

Continuing the example, the work cell includes a first instrument and a second instrument. A work cell may include unique instruments of different types, or may include multiple instruments of the same type with or without an instrument of a different type. For example, the first instrument may be a hematology analyzer, and a second instrument may be an imaging system. As another example, the first instrument may be a hematology analyzer, and the second instrument may be a slide maker and/or slide stainer. As another example, the first instrument may be a particle morphology analyzer and the second instrument may be a particle counter. For example, a work cell may include two hematology analyzers and an imaging system. In some cases, quality control specimens can be placed in a cassette with other patient specimens, although this may not be preferred practice in some situations.

Continuing the example, the first instrument may detect that a quality control specimen is present and performs a quality control test. The quality control specimen may be identified by a machine-readable bar code or other machine-readable marking, including, without limitation, text, or may be identified based on a specimen container (such as a tube or disc) or specimen cassette that is unique to quality control specimens. If the quality control test fails, the failure may cause the first instrument to cease processing tests. In this manner, results that could be incorrect are not released to the patient or physician. Rather, any patient specimens are flagged for retesting subsequent to a passing quality control test. The first instrument then re-runs the quality control specimen by performing the test a second time. There may be a delay between analyzing a quality control specimen and determining, e.g., by a processor, that the result of the quality control test was outside the expected tolerance. If any patient specimens were testing during this delay, those patient specimens may be retested. In a work cell including multiple instruments of the same type, if a first instrument fails a quality control test and a second instrument passes a quality control test, testing of patient specimens may continue on the second instrument while the first instrument is not processing specimens. In a work cell including multiple instruments of different types, if a first instrument fails a quality control test and the second instrument passes a quality control test, a patient specimen that was analyzed using both instruments may be retested in only the first instrument.

In a second example, an instrument detects that a cassette includes one or more patient specimens in conjunction with a quality control specimen. The detection can be accomplished, for example, by the instrument scanning a bar code on the quality control specimen. The instrument may send an alert or and rejects the cassette before any processing takes place. The instrument may send the cassette to the output buffer. Isolating quality control specimens from patient specimens may help limit the number of specimens that have to be retested following a failed quality control test and/or may facilitate automated retrieval of specimens for retesting (quality control specimens, patient specimens, or both).

Figure 1:
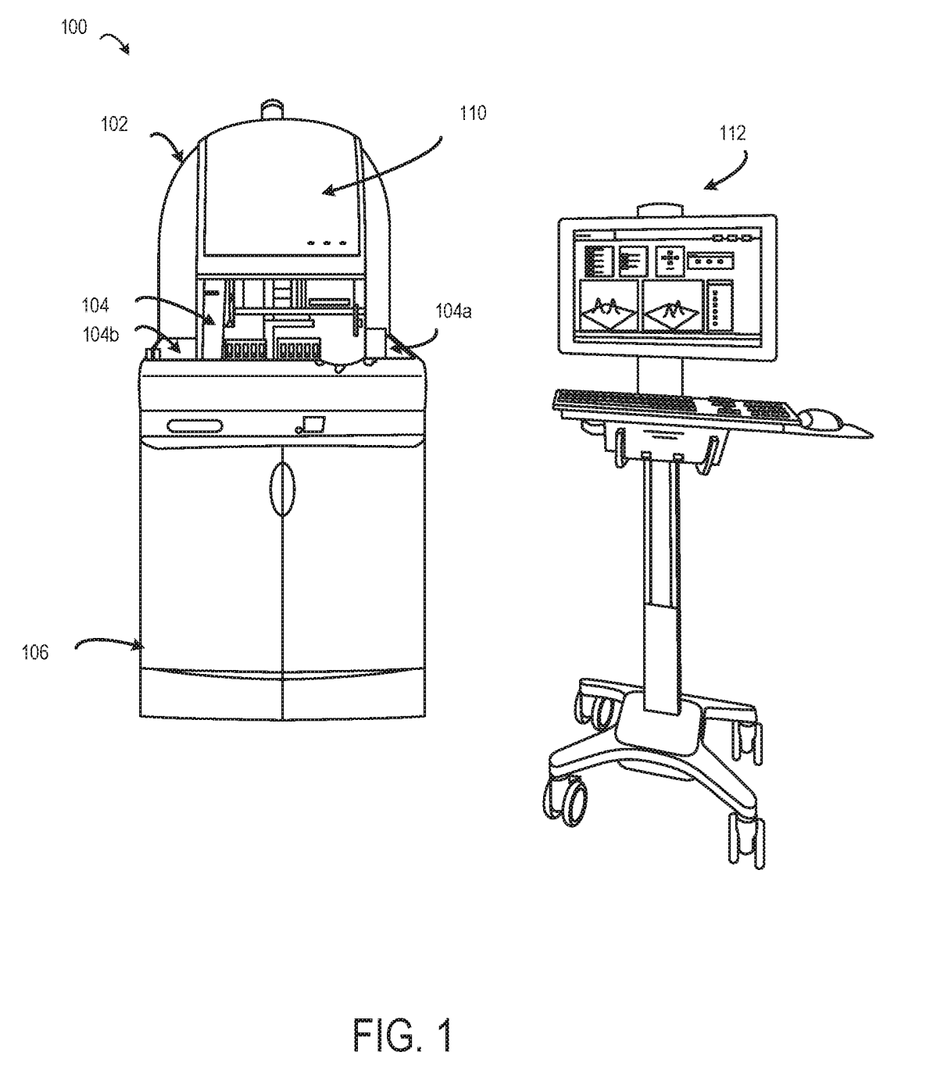
FIG. 1 depicts a front perspective view of a laboratory instrument, according to an aspect.

FIG. 1 depicts a front perspective view of a laboratory instrument 100. Instrument 100 receives patient specimens, performs tests such as blood analysis, urine analysis, body fluid analysis (e.g., cerebrospinal fluid, pleural fluid, or synovial fluid) and the like, and provides the results to a laboratory technician, LIS, clinician, or other entity.

Instrument 100 includes a housing 102 with sides defining the front, back, left and right sides, top and bottom as illustrated. Instrument 100 can include a horizontal working deck 104 that incorporates readily accessible areas for an operator to add specimens for analysis and consumables for use in processing the specimens. Working deck 104 can include an input buffer 104a, where the specimens are provided, and an output buffer 104b, where the processed specimens are collected.

Instrument 100 can also include a transport shield 110 that restricts operator access to specimens when instrument 100 is operating. Instrument 100 can also include a storage location 106. Storage location 106 can include space for supplies such as quality control specimens, and can also provide technician access to the inner workings of instrument 100. Instrument 100 can include or receive consumables such as reagents for performance of a variety of functions, including, for example, specimen preparation and instrument flushing or cleaning. Sufficient storage space for consumables can be provided on the system, permitting operation with minimal operator intervention for an extended time.

Instrument 100 also includes one or more computing systems 112 that can be used for data entry, analysis, quality control, or calibration. An example computing system is shown in more detail in FIG. 8. Computing system 112 can be programmed to execute the quality control functions such as detecting when a quality control test has failed, identifying which instrument(s) in a work cell failed a quality control test, re-starting a quality control test, causing the instrument 100 to cease processing other specimens, redirecting patient specimens from an instrument in a work cell that has failed a quality control test to an instrument in a work cell that has passed a quality control test, and reporting the results, e.g., via the display, status light, via an electronic message, or a message to the LIS.

In one aspect, the computing system 112 can be external to instrument 100 (as shown) and connected via wireless or wired connection. In another aspect, the computing system 112 can be part of the instrument 100. Instrument 100 can include a light or a speaker to provide alerts to an operator. Alerts can indicate that a quality control test failed or that operator intervention is needed. For example, instrument 100 may include a light that changes to red in the event of a quality control issue that has stopped the instrument from operating, yellow for a warning, or green to indicate correct operation. An additional light, such as a blue or purple light, could be used to indicate that the instrument is ready to run but is not currently processing specimens, for example, because the instrument has analyzed all of the specimens in the input buffer 104a. Computing system 112 can connect to a remote device that can receive uploaded parameters from the instrument or receive commands such as initiating further quality control testing or diagnostics.

Instrument 100 can be a single, enclosed system. For example, instrument 100 can receive specimens, perform tests, and output the specimens and results in isolation. Alternatively, instrument 100 can operate in conjunction with other instruments as a work cell, as further described with respect to FIG. 2. Instrument 100 can detect a presence of a quality control specimen by scanning a bar code or other marking present on the specimen. In addition to or in lieu of a bar code or special marking, quality control specimens could be identified by cassettes or specimen containers of a size, shape, color or other aspect distinguishable from patient specimens. For example, quality control specimens could be presented in a tube that is taller than patient specimen tubes, or has a tube cap of a different color, size or surface texture from a patient specimen tube, such that the quality control specimens could be recognized by visual analysis. Instrument 100 may include markings to facilitate distinguishing different specimen tubes, e.g., a mark that is visible above some kinds of specimen containers but obscured by a portion of a different kind of specimen container.

Figure 2:
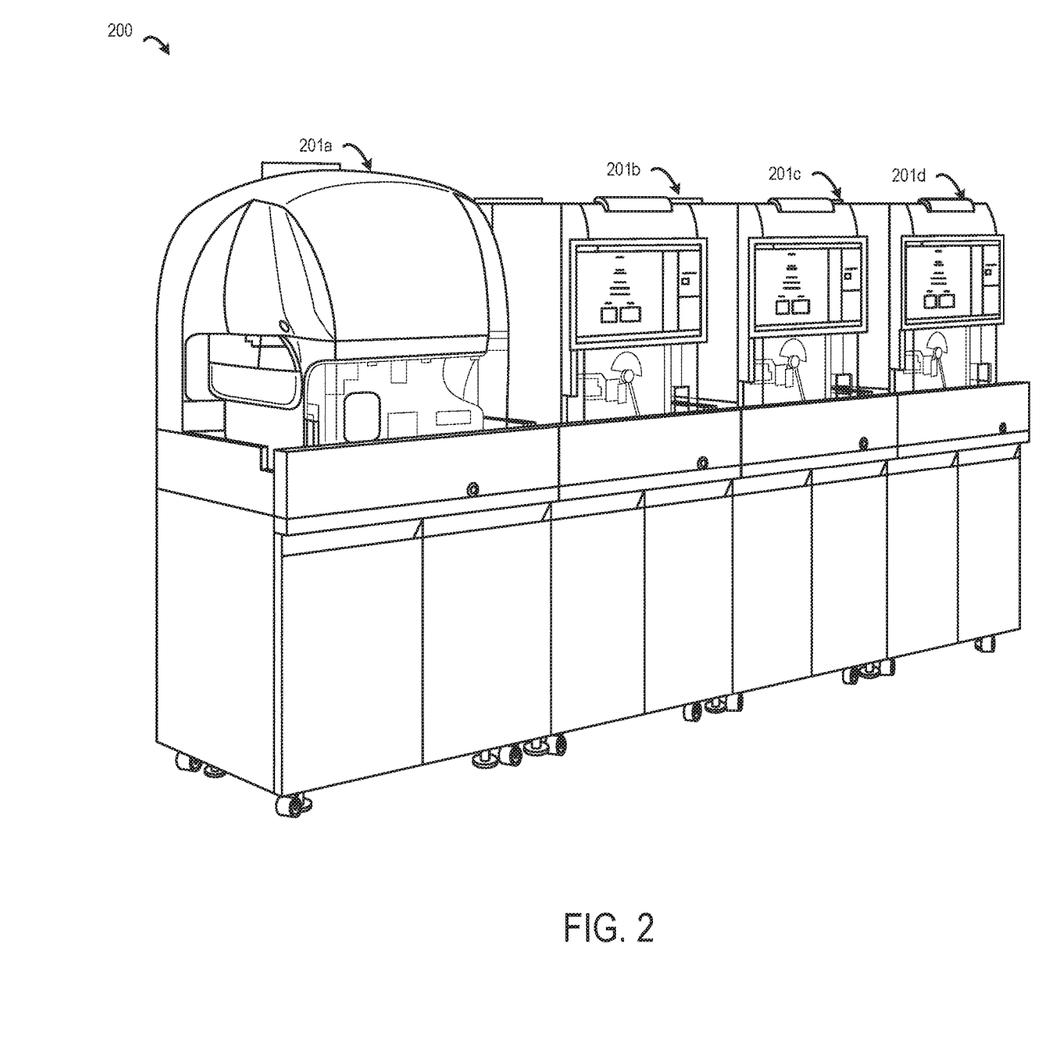
FIG. 2 depicts multiple laboratory instruments interconnected to form a work cell, according to an aspect.

FIG. 2 depicts multiple laboratory instruments interconnected to form a work cell 200. Work cell 200 includes two or more instruments connected in series to form a pipeline. Work cell 200 includes instrument 201a, instrument 201b, instrument 201c, and instrument 201d. Each instrument 201a-d can perform a different test. Instruments 201 a-c need not look the same. For example, as depicted, instrument 201a has a particular look and feel, whereas instruments 201b-d have another look and feel. Work cell 200 can provide the results of multiple tests in one aggregated report. Instruments 201a-c can be of the same type, e.g., three hematology analyzers, or could be of different types, e.g., a combination of two or more of hematology analyzers, particle counters, urine analyzers, flow cytometers, imaging devices, slide makers, slide stainers, and the like.

Depending on the types of instruments included in work cell 200, there may be a logical order for the instruments. For example, a hematology analyzer or particle counter may be the first-in-time instrument to which a specimen is directed, and if the results of the hematology analysis or particle counting require human review, the specimen may be directed to an imaging device or slide maker. In other circumstances, there may be no logical order for the instruments. For example, the work cell may include multiple instruments of the same type, such as two or three hematology analyzers. In some circumstances, the work cell may include a transport mechanism, such as a robotic arm, that operates to move specimens between the individual instruments in the work cell such that the instruments do not physically need to reside in any particular spatial or temporal order.

Work cell 200 includes an input buffer (depicted in FIG. 1 as 104a) that receives cassettes of specimens. Work cell 200 provides the cassette to the first instrument, e.g., instrument 201a. Instruments 201a-d form a work flow or a pipeline of instruments such that after a specimen is provided to the input buffer of work cell 200, the specimen may be tested multiple times, each using a different test. For example, instrument 201a can test a specimen for a blood cell count and pass the specimen to instrument 201b that tests the same specimen for blood chemistry, and so on. As another example, instrument 201a can test a specimen for a blood cell count, and the following work flow may be modified based on the result of the first test, with the specimen being passed to the output buffer 104b if the first test generates certain results, such as results within expected tolerances or results indicating a problem with the specimen or the equipment, and with the specimen being passed to instrument 201b, 201c, and/or 201d if the first test generates other results, such as one or more results outside of expected tolerances, or if additional tests have been ordered for a particular specimen. The tests ordered for a particular specimen may be associated with a barcode or other marking on the specimen container. Work cell 200 also includes an output buffer (depicted in FIG. 1 as 104b) that receives the cassettes that have been processed by each instrument 201a-d or that have been rejected, for example due to mixing quality control specimens with patient specimens.

Each instrument 201a-d can perform quality control. The quality control tests for a particular instrument 201a-d can be the same or different relative to other instruments within the work cell. Each test may use an identical quality control specimen or different quality control specimens. Accordingly, each instrument 201a-d is interconnected via a communications interface to enable the status of quality control tests and other diagnostic information can be shared among devices. Alternatively, a central device or processor can collect diagnostic information.

Instruments 201a-d can include one or more computing systems. The computing device, as further described with respect to FIG. 8, can perform management of an instrument or multiple instruments. The computing device is configurable to control operations of an instrument such as initiating testing of patient specimens, checking correct operation, sending results to clinicians, sending alerts to laboratory technicians, and executing quality control procedures.

Any of instruments 201a-d can initiate quality control procedures on any other instrument 201a-d. For example, one instrument can be a designated controller that handles quality control testing and retesting. The controller can issue commands to the other instruments. In another example, an external computing device can automate testing and retesting for the instruments 201a-d.

Figure 3:
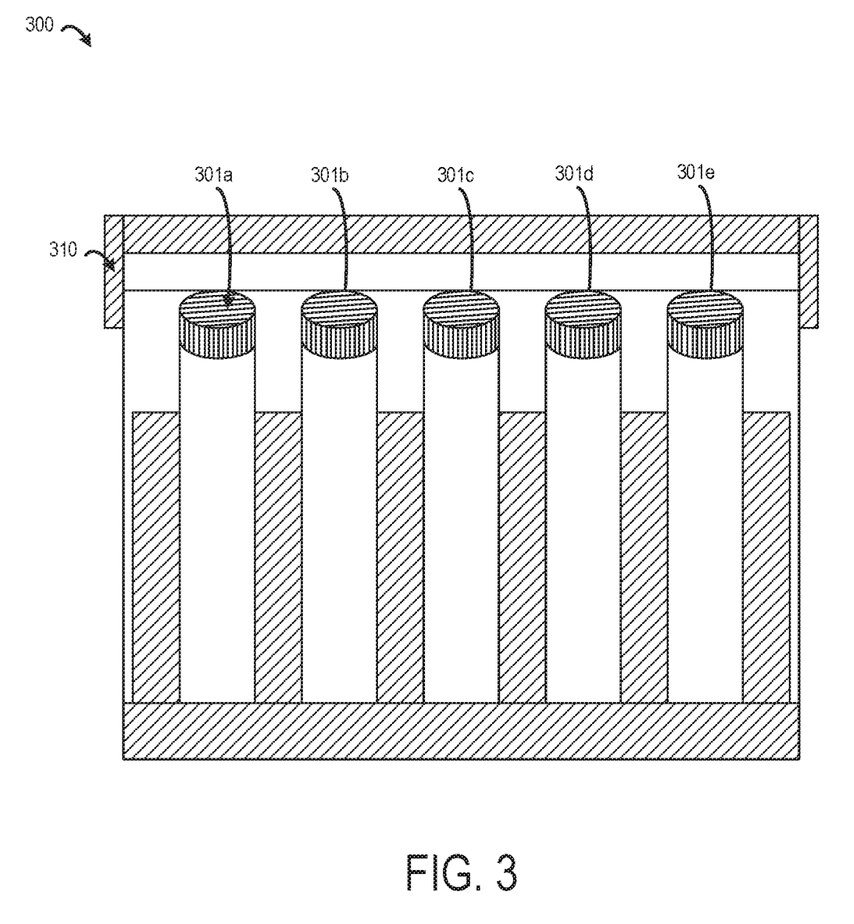
FIG. 3 depicts a cassette for storing laboratory specimens, according to an aspect.

FIG. 3 depicts a cassette 300 for storing laboratory specimens. Cassette 300 includes specimen storage locations 301a-e and support structure 310. Five specimen storage locations are shown, but any number of storage locations is possible. Cassette 300 can store patient specimens, quality control specimens, or both. Instrument 100 or instruments 201a-d can process specimens in cassette 300.

Laboratory instruments can identify a specimen by scanning a barcode or other identifying indicia on the specimen. The identifying indicia could include a marking, such as a barcode, including matrix and 3-D barcodes, text or non-text symbols, or could be defined by a feature of the specimen container holding the specimen. For example, a quality control specimen might be presented in a specimen container of different dimensions than a patient specimen (e.g., a taller tube or a shorter tube), or might be presented in a tube with different optical or surface properties than a patient specimen (e.g., a colored, frosted, or transparent container, or containers with combinations of coloring, frosting and/or transparency, surface modifications such as scoring, etching, or rolled patterning, or might be presented in a tube with a different cap, such as a cap of a different color, size, shape, or surface texture (e.g., ridged, smooth, ridged horizontally vs. ridged vertically, etc.). Combinations of indicia could be used, such as a surface pattern which serves as a "marking" with a symbol or pattern of symbols.

Figure 4:
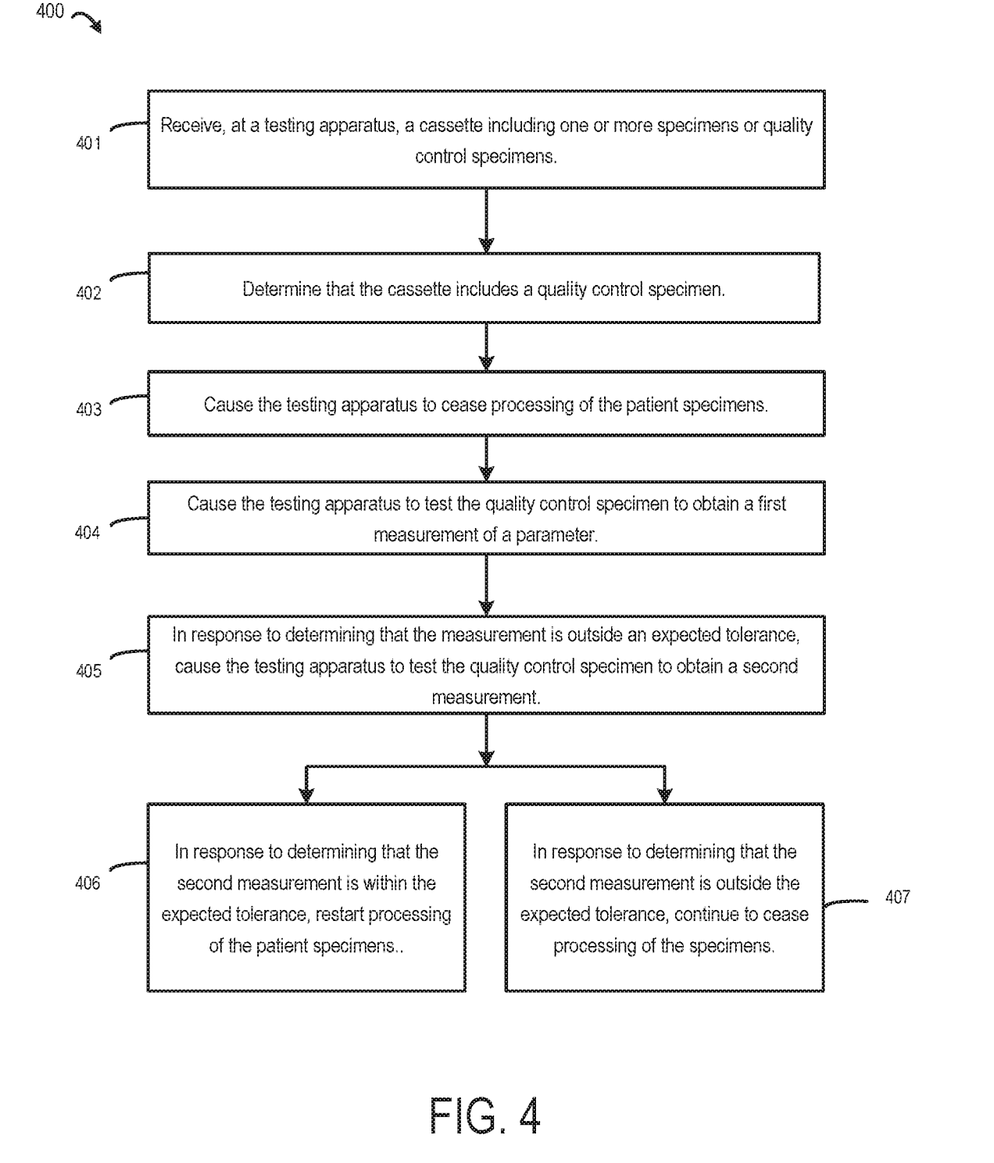
FIG. 4 depicts a flowchart illustrating an example of a process for performing quality control of an instrument.

FIG. 4 depicts a flowchart illustrating an example of a process 400 for performing quality control. Process 400 can be implemented by instrument 100, or instruments 201a-d, an external processing device, or other suitable processing devices. Process 400 can cause an instrument, or testing apparatus, to perform various functions.

Figure 5:
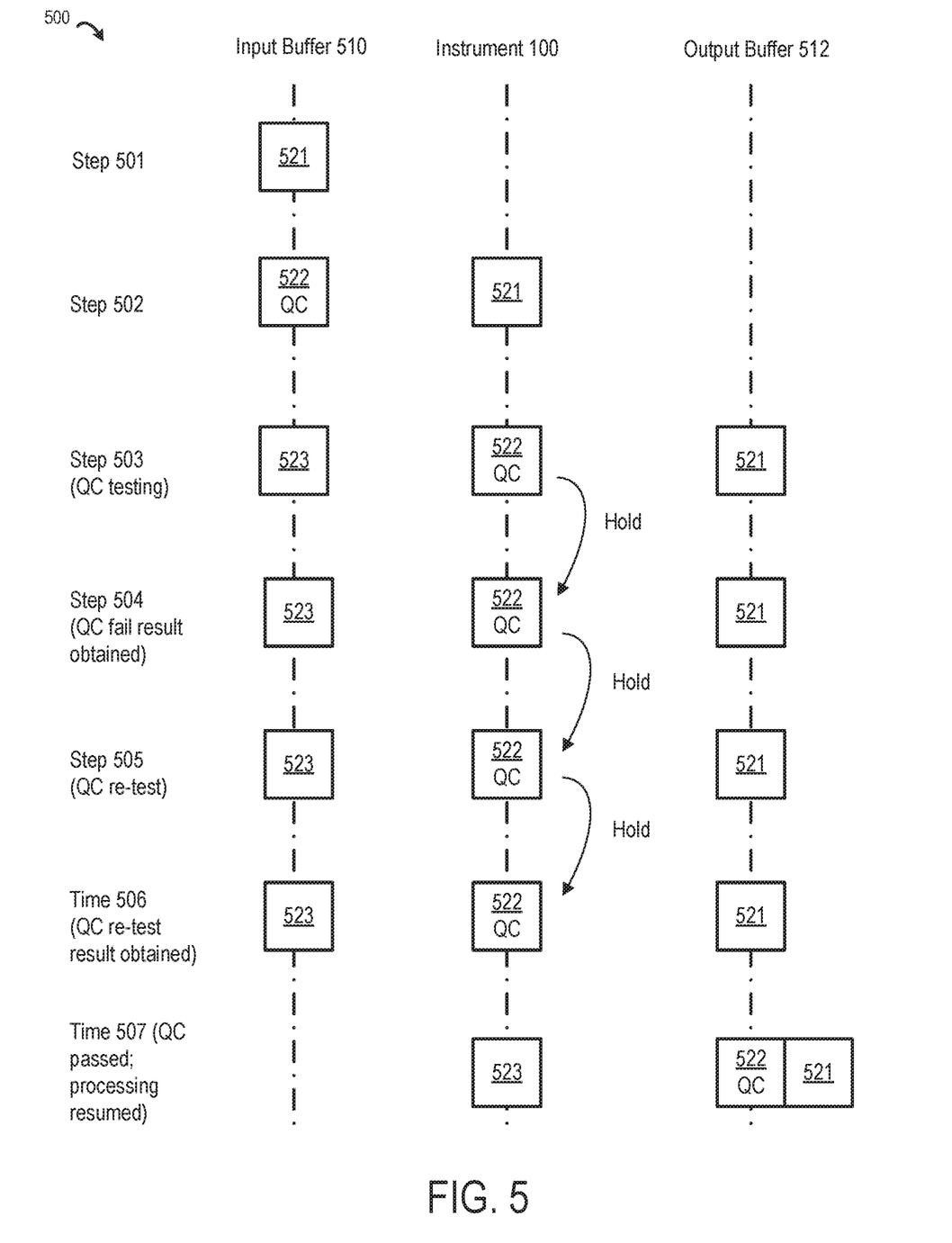
FIG. 5 depicts an example timeline for specimen processing as implemented by the process in FIG. 4.

For illustrative purposes, FIG. 4 is described with respect to FIG. 5. FIG. 5 depicts an example timeline 500 for specimen processing as implemented by the process in FIG. 4. FIG. 5 depicts steps 501-505, input buffer 510, instrument 100, and output buffer 512. Steps 501-505 occur in sequence and depict steps in time as specimens move from input buffer 510 to instrument 100 for testing, to output buffer 512. FIG. 5 also depicts three cassettes: cassette 521, control cassette 522, and cassette 523. Each cassette includes one specimen. Cassette 522 includes a quality control specimen and is presented after cassette 521 but before cassette 523 in a testing sequence.

Returning to FIG. 4, at block 401, process 400 involves receiving, at a testing apparatus, a cassette including one or more patient specimens or quality control specimens. For example, cassette 522 is placed in input buffer 510 by a lab technician. Instrument 100 receives cassette 522 and positions the cassette for testing. As depicted at step 502, cassette 522 is in input buffer 510 and cassette 521, previously inserted in input buffer 510, has moved to instrument 100.

At block 402, process 400 involves determining that the cassette includes a quality control specimen. Continuing the example, instrument 100 uses a scanner to scan a bar code or any other identifying indicia on cassette 522. Instrument 100 compares the scanner result with a data structure and determines that cassette 522 includes a quality control specimen. As depicted at step 503, the quality control specimen is inside instrument 100 for testing. Additionally, at step 503, cassette 521 is in output buffer 512 and cassette 523, behind cassette 522, is at input buffer 510.

At block 403, process 400 involves causing the testing apparatus to cease processing of the cassettes. Instrument 100 refrains from processing patient specimens and holds cassette 522 (and therefore the quality control specimen) inside the machine. As depicted at step 503, processing is held and the cassette 522 remains in instrument 100 until the quality control test result is obtained.

In an aspect, instrument 100 may also eject any cassettes already present within the instrument or move the cassettes to an output buffer.

At block 404, process 400 involves causing the testing apparatus to test cassette 522 to obtain a first measurement of a parameter. Instrument 100 aspirates the specimen from cassette 522 and performs the quality control test. As depicted in step 504, cassette 522 remains in place and is not propagated forward to another instrument or the output buffer. No other processing takes place.

At block 405, process 400 involves, in response to determining that the measurement is outside an expected tolerance, activating an alert or causing the testing apparatus to test the quality control specimen to obtain a second measurement. As depicted in step 505, instrument 100 re-tests cassette 522. During retesting, processing of patient specimens remains stopped.

At block 406, process 400 involves, in response to determining the second measurement is within the expected tolerance, restarting processing of cassette 522. As depicted in step 506, instrument 100 obtains the second quality control result. If the result indicates a pass, processing resumes as depicted in step 507. In the case of a work cell, the quality control specimen is routed to the next instrument in the work cell for quality control testing to take place on the next instrument.

At block 407, process 400 involves, in response to determining that the second measurement is outside the expected tolerance, continuing to cease processing of the specimens. If the result indicates a fail, then instrument 100 can cease processing of cassettes and send an alert to notify operator that instrument 100 is possibly out-of-calibration. Alerts can include a beacon light, sent to a central computer terminal, or sent directly to a human operator via SMS, text, e-mail, automated phone message, pager, etc. Continuing the example in FIG. 5, cassette 523 is not processed. Instrument 100 can eject cassette 523 pending repair or recalibration of instrument 100.

Figure 6:
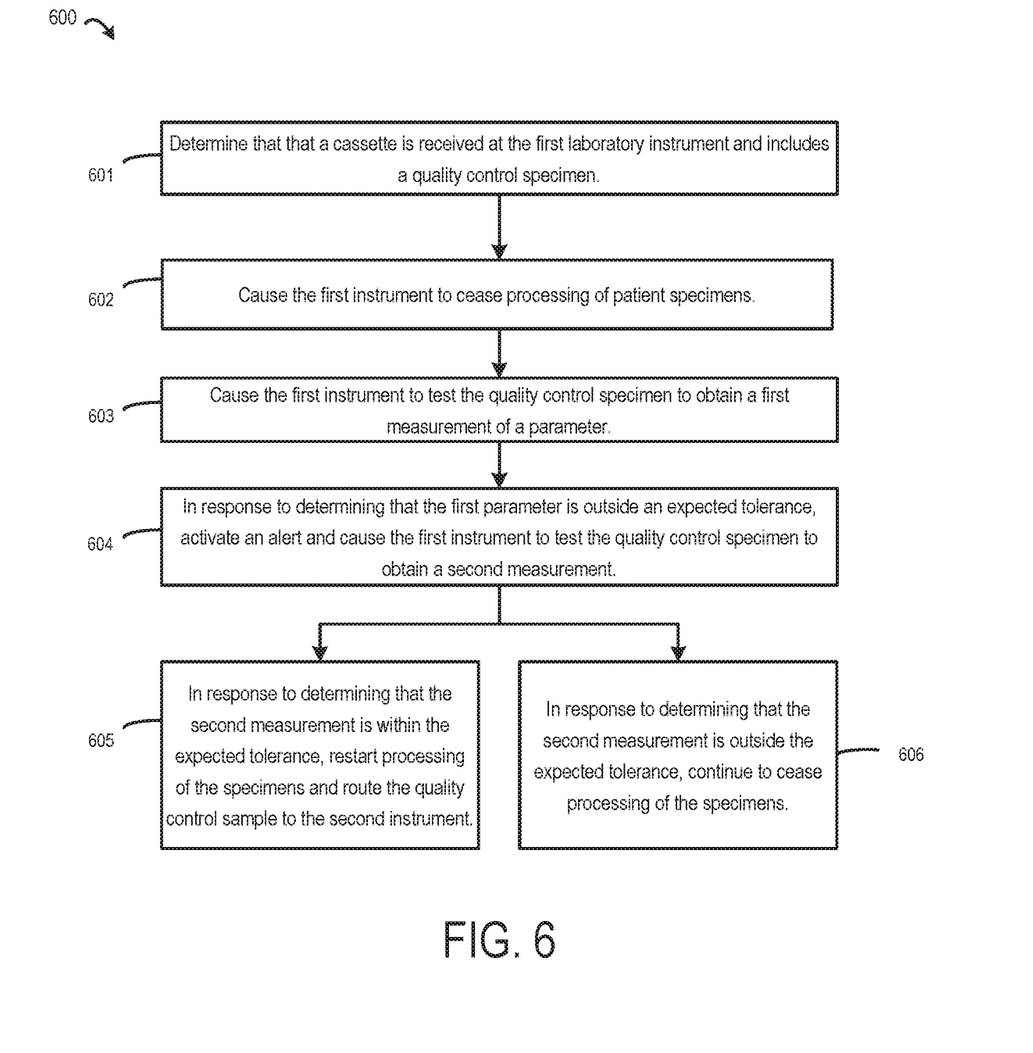
FIG. 6 depicts a flowchart illustrating an example of a process for performing quality control within a work cell.

FIG. 6 depicts a flowchart illustrating an example of a process 600 for performing quality control within a work cell. Process 600 can be implemented by a processor within any of the instruments 201a-d, an external processing device, or other suitable processing devices. For example purposes, instrument 201a is described as performing process 600. Quality control can be performed separately on each instrument 201a-d.

At block 601, process 600 involves determining that a cassette is received at the first laboratory instrument and includes a quality control specimen. At block 601, instrument 201a performs substantially similar operations as in block 402 of process 400.

At block 602, process 600 involves causing the first instrument to cease processing of patient specimens. Instrument 201a causes the instrument 201a to refrain from specimen processing and ejects any specimens already present within instrument 201a.

At block 603, process 600 involves causing the first instrument to test the quality control specimen to obtain a first measurement of a parameter. For example, instrument 201a aspirates the specimen and performs the quality control test to obtain the first measurement.

At block 604, process 600 involves, in response to determining that the first parameter is outside an expected tolerance, activating an alert or causing the first instrument to test the quality control specimen to obtain a second measurement. Instrument 201a re-tests the quality control specimen. Specimen processing remains held.

Subsequent to block 604, the work cell executes either block 605 or block 606. If the second measurement is within the expected tolerance, then the work cell executes block 605. If the second measurement is outside the expected tolerance, then the work cell executes block 606.

At block 605, process 600 involves, in response to determining that the second measurement is within the expected tolerance, restarting processing of the patient specimens, if any, queued for testing in instrument 201a. The instrument routes the cassette that contains the quality control specimen to the second instrument, where the quality control specimen is tested.

At block 606, process 600 involves, in response to determining that the second measurement is outside the expected tolerance, continuing to cease processing of the specimens. This functionality can be referred to as "auto-stop," indicating an automatic stopping of processing subsequent to a second failing quality control test. In an aspect, instrument can automatically move such specimens to the input buffer for retesting after the quality control failure is resolved. In some aspects, the processor may cause a patient specimen with potentially erroneous results to be retested on a different instrument within the work cell than the instrument which failed the quality control test. The instrument can send a notification to a manufacturer, vendor, lab technician or other operator or service provider who may be responsible for resolving the quality control failure. In another aspect, an instrument that fails quality control a second time can continue to process specimens if an operator disables the auto-stop functionality.

In conjunction with processes 400 or 600, or separately, instruments disclosed herein can determine a presence of a mixed cassette. Mixed cassettes are cassettes that include a quality control specimen and a patient specimen.

Figure 7:
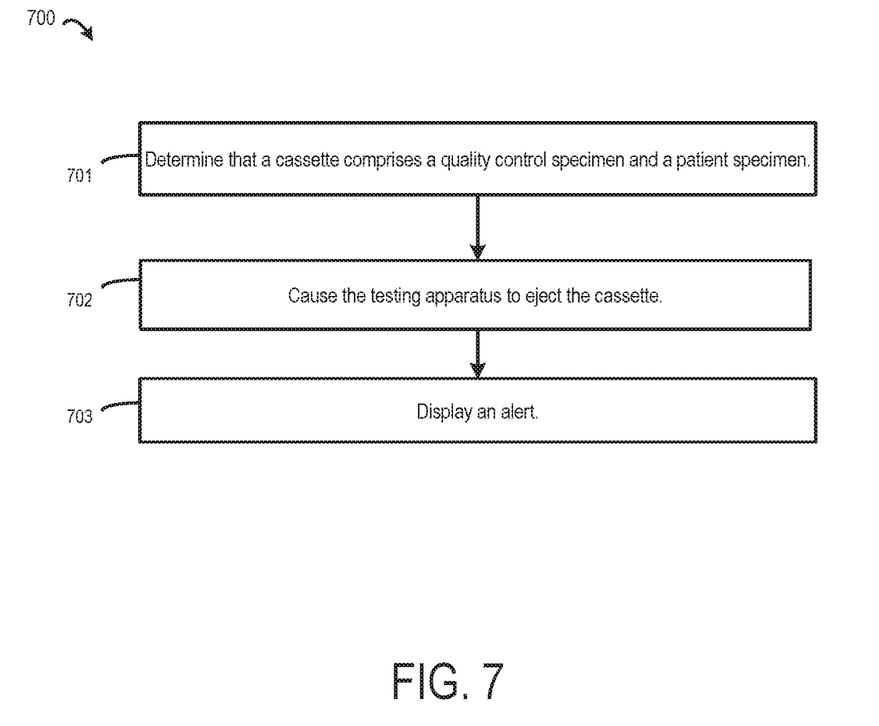
FIG. 7 depicts a flowchart illustrating an example of a process for rejecting mixed cassettes presented to an instrument.

FIG. 7 depicts a flowchart illustrating an example of a process for rejecting mixed cassettes presented to an instrument. Mixed cassettes can cause problems for laboratory instruments because the patient specimen contained within the cassette may need to be retested pending quality control results obtained from testing the quality control specimen. Once a specimen is aspirated, the instrument can automatically process the specimen. For example, an instrument may have aspirated a patient specimen, tested the specimen, and output the results before the quality control specimen has completed processing. Therefore, in the event that the quality control specimen fails, the patient specimen may need to be re-tested as testing has already taken place once. Hence, by stopping processing of mixed cassettes, disclosed solutions provide advantages by avoiding releasing results from patient specimens in a cassette that contains a quality control specimen. Process 700 can be implemented by instrument 100 or any of instruments 201*a-d*.

At block 701, process 700 involves determining that a cassette comprises a quality control specimen and a patient specimen. For example, the instrument scans a bar code or other identifying indicia on the quality control specimen, thereby detecting the presence of a quality control specimen. The instrument then scans a bar code or other identifying indicia on a patient specimen, thereby detecting a presence of at least one patient specimen.

At block 702, process 700 involves causing the testing apparatus to eject the cassette. The instrument may eject the cassette to the output buffer, for example.

At block 703, process 700 involves displaying an alert. The alert can be displayed on a display device or sent to an operator by another electronic means such as a message. For example, the instrument illuminates a red light on the instrument and sends an alert such as a message or email. The alert informs laboratory personnel that the cassette needs to be placed back in the input buffer for retesting after removing any patient specimens in the cassette.

Exemplary Computing Device

Figure 8:
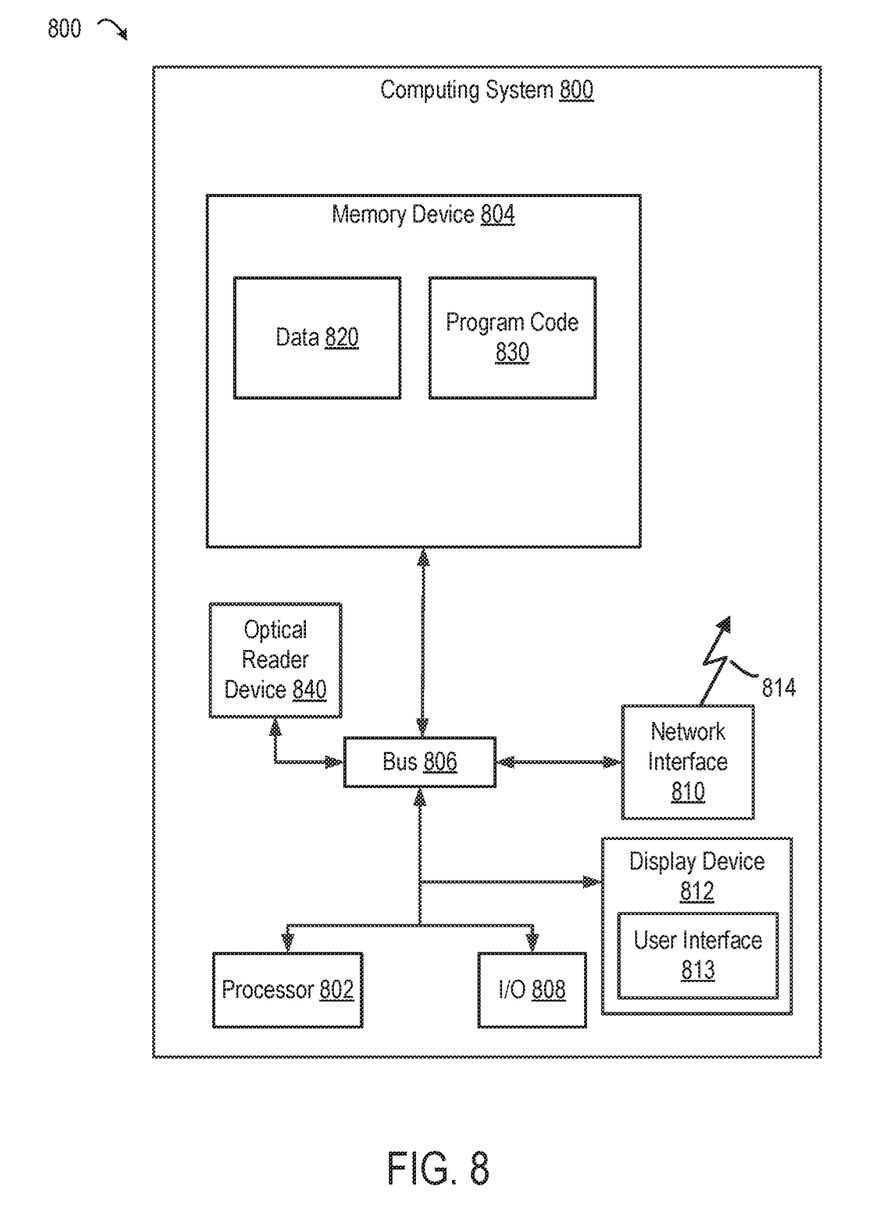
FIG. 8 depicts an exemplary computing system for instrument operation and testing.

FIG. 8 depicts an exemplary computing system for instrument operation and testing. Any suitable computing system may be used for performing the operations described herein. The depicted example of a computing device 800 includes a processor 802 communicatively coupled to one or more memory devices 804. The processor 802 executes computer-executable program code 830 stored in a memory device 804, accesses data 820 stored in the memory device 804, or both. Examples of the processor 802 include a microprocessor, an application-specific integrated circuit ("ASIC"), a field-programmable gate array ("FPGA"), or any other suitable processing device. The processor 802 can include any number of processing devices or cores, including a single processing device. The functionality of the computing device may be implemented in hardware, software, firmware, or a combination thereof.

The memory device 804 includes any suitable non-transitory computer-readable medium for storing data, program code, or both. A computer-readable medium can include any electronic, optical, magnetic, or other storage device capable of providing a processor with computer-readable instructions or other program code. Non-limiting examples of a computer-readable medium include a flash memory, a ROM, a RAM, an ASIC, or any other medium from which a processing device can read instructions. The instructions may include processor-specific instructions generated by a compiler or an interpreter from code written in any suitable computer-programming language, including, for example, C, C++, C#, GI, Visual Basic, Java, or scripting language.

The computing device 800 may also include a number of external or internal devices, such as input or output devices. For example, the computing device 800 is shown with one or more input/output ("I/O") interfaces 808. An I/O interface 808 can receive input from input devices or provide output to output devices. One or more busses 806 are also included in the computing device 800. The bus 806 communicatively couples one or more components of a computing device 800.

The computing device 800 executes program code 830 that configures the processor 802 to perform one or more of the operations described herein. For example, the program code 830 causes the processor to perform the operations described in FIG. 4, 6, or 7.

The computing device 800 also includes a network interface device 810. The network interface device 810 includes any device or group of devices suitable for establishing a wired or wireless data connection to one or more data networks. The network interface device 810 may be a wireless device and have an antenna 814. The computing device 800 can communicate with one or more other computing devices implementing the computing device or other functionality via a data network using the network interface device 810.

The computing device 800 can also include a display device 812. Display device 812 can be a LCD, LED, touch-screen or other device operable to display information about the computing device 800. For example, information could include an operational status of the computing device, network status, etc. Display device 712 can include user interface 713. User interface 713 can be any user interface such as a graphical user interface (GUI) that can display text, graphics, icons, visualizations, and the like.

The computing device 800 can also include optical reader device 840. Optical reader device 840 can be any optical recognition device such as a camera that can be configured to read and process a barcode or another visual marking on a specimen, label, or other printed material. Optical reader device 840 provides a scanned code to processor 802, which can process the code, for example, by accessing a table to determine any embedded parameters in the code such as name, identification number, specimen number, whether the specimen is a quality control specimen, etc.

In the preceding description, for the purposes of explanation, numerous details have been set forth in order to provide an understanding of various aspects of the present technology. It will be apparent to one skilled in the art, however, that certain aspects may be practiced without some of these details, or with additional details, or in varied combinations or sub-combinations of features of the aspects.

Having described several aspects, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific aspect may not always be present in variations of that aspect or may be added to other aspects.

As used herein, the terms "first," "second," "third," etc. refer to examples and are not limited in spatial or temporal order. For example, a "first" device need not occur first in a sequence. Similarly, a "second" object need not be placed after a "first" object and before a "third" object.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the transducer" includes reference to one or more transducers and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A method for quality control of a hematology laboratory instrument, the method comprising:
    ejecting a cassette received from an input buffer in a case wherein a processor determines that the cassette is a mixed cassette that comprises both a quality control specimen and a patient specimen, wherein the processor is configured to cause the ejection of the cassette responsive to the determination that the cassette is the mixed cassette;
    the processor further configured to:
    determining that the cassette includes the quality control specimen;
    in a case wherein the cassette includes the quality control specimen, does not include the patient specimen, and is not ejected, testing the quality control specimen with a first testing apparatus to obtain a first measurement of a parameter;
    responsive to determining that the first measurement is outside an expected tolerance:
        causing the first testing apparatus to cease performing tests on additional patient specimens from one or more additional cassettes comprising ceasing tests in progress on the additional patient specimens and/or ceasing tests to be performed on the additional patient specimens that are in the input buffer, and testing the quality control specimen to obtain a second measurement; and
    responsive to determining the second measurement is within the expected tolerance:
        restarting the tests in progress on the additional patient specimens and/or the tests to be performed on the additional patient specimens that are in the input buffer; and
    responsive to determining the second measurement is outside the expected tolerance:
        continuing to cause the first testing apparatus to cease the tests in progress on the additional patient specimens and/or to be performed on the additional patient specimens that are in the input buffer.

2. The method of claim 1, further comprising:
    sending an alert; or
    displaying an alert on a display device in response to determining that the first measurement is outside the expected tolerance.

3. The method of claim 1, wherein determining that the cassette includes a quality control specimen comprises reading a bar code or other identifying indicia on the quality control specimen.

4. The method of claim 1, wherein determining that the cassette includes the quality control specimen comprises allowing the tests in progress on the additional patient specimens to continue.

5. The method of claim 1, wherein determining that the cassette includes the quality control specimen and the patient sample comprises identifying a first tube comprising the quality control specimen that is taller than a second tube comprising the patient sample.

6. The method of claim 1, wherein determining that the cassette includes the quality control specimen and the patient sample comprises identifying a tube cap on a first tube comprising the quality control specimen that has a different surface texture than that of a tube cap on a second tube comprising the patient sample in the cassette.

7. The method of claim 1, wherein causing the first testing apparatus to cease the tests in progress and/or to be performed on the additional patient specimens comprises causing the first testing apparatus to cease the tests to be performed on the additional patient specimens that are in the input buffer, the method further comprising:
    transferring the additional one or more cassettes comprising the additional patient specimens from the input buffer to a second testing apparatus; and
    performing the tests to be performed on the additional patient specimens from the input buffer using the second testing apparatus.

8. The method of claim 1, comprising performing the method wherein the cassette comprises the mixed cassette and is ejected, and further comprising performing the method again wherein the cassette does not comprise both the quality control specimen and the patient specimen.

* * * * *